United States Patent [19]

Haissig et al.

[11] 4,297,125

[45] Oct. 27, 1981

[54] TREE ROOTING USING SYNTHETIC AUXINS

[75] Inventors: Bruce E. Haissig, Rhinelander, Wis.; Jack R. Gaines, Rapid City, S. Dak.; Glen Giacoletto, Richland, Wash.

[73] Assignee: The United States of America as represented by the Secretary of Agriculture, Washington, D.C.

[21] Appl. No.: 52,656

[22] Filed: Jun. 27, 1979

[51] Int. Cl.$^3$ ............................................. A01N 21/00
[52] U.S. Cl. ................................. 71/77; 260/326.13 B
[58] Field of Search ............................................. 71/77

[56] References Cited

U.S. PATENT DOCUMENTS 2,204,213  6/1940  Grace ..................................... 71/77

OTHER PUBLICATIONS

Haissig, Plant Physiology (Supplement), 61(4):65, (1978).

Primary Examiner—Paul M. Coughlan, Jr.
Attorney, Agent, or Firm—M. Howard Silverstein; David G. McConnell

[57] ABSTRACT

Aryl esters of auxins, such as phenyl indole-3-butyrate, are found to significantly improve the initiation of rooting of cuttings is difficult-to-root species, such as *pinus*.

7 Claims, No Drawings

TREE ROOTING USING SYNTHETIC AUXINS

FIELD OF THE INVENTION

The present invention relates to the stimulation of adventitious root formation in cuttings, and more particularly to the use of synthetic auxins to initiate adventitious root formation.

BACKGROUND OF THE INVENTION

The naturally occuring auxin indole-3-acetic acid (hereinafter IAA) was shown shortly after its discovery to stimulate adventitious root formation in cuttings of the easy-to-root plants, also called "good rooters" (see Went et al. 1937. Phytohormones. Mac Millan Co., N.Y. 294p). Synthetic auxins such as indole-3-butyric acid (IBA) and Naphthalene-acetic acid (NAA) have more effectively induced rooting in cuttings, particularly cuttings of difficult-to-root species also call "poor rooters" (see Audus, 1959, Plant growth substances, 2nd Ed. Interscience Pub, Inc. N.Y. 553p; also see Hartmann et al. 1975).

However, cuttings from many species of plants remain difficult to root because they do not respond to known formulations of auxins, of which many have been tested (Audus, supra). Mature trees in general, particularly of certain commercially important types, are an important class of plants that remain difficult or impossible to propagate economically.

Simple phenolics when administered with an auxin sometimes cause a synergistic response in adventitious root initiation (Haissig. 1974. Influences of auxins and auxin synergists on adventitious root primidium initiation and development ment. N.Z.J. For. Sci. 4: 311–323). Several theories have been proposed to explain the synergism, one theory being that auxin molecules become bonded to the phenolic moiety, and that the conjugate induces root initiation more effectively than either chemical separately (Haissig,supra). Methyl or ethyl esters of auxins have sometimes been shown to enhance adventitious root initiation better than free acids (Veldstra. 1944. Researches on plant growth substances, Enzymologia II, 97–163). The naturally occuring auxin IAA sometimes appears naturally esterified to other compounds (Schantz. 1966. Chemistry of naturally occuring growth regulating substances. Ann, Rev. Plant Physiol. 17: 409–438), and poorly defined auxin-phenolic conjugates have been reported.

Among the known auxins, IAA does not appear to work as a rooting hormone on woody, as opposed to herbaceous, cuttings at all. All commercially available rooting hormone preparations comprise IBA, naphthylene acidic acid (NAA), amides of naphthylene acidic acid, mixtures of the foregoing, or mixtures of the foregoing with IAA. These materials have all been available for many years, but they are generally unsatisfactory for "poor rooters" and "non-rooters" and nothing better has appeared over the years, in spite of the need for effective rooting hormones for such poor rooters and non-rooters. Thus, Dr. Hudson T. Hartmann, Head of the Pomology Department at the University of California (Davis) has stated: "No growth regulators useful in stimulating production of adventitous roots on cuttings that are better than the long standard indolebutyric acid and napthaleneacetic acid are appearing." (New Vistas in Plant Propagation. International Plant Propagators Society Combined Proceedings. 27:106–113 (1977).

It has been reported [Haissig. 1978. Influence of phenyl indole-3-acetate on adventitious root premordium initiation and development. Plant Physiology (Supplement) 61(4):65. (Abstract of paper presented at the annual Meeting of the Am. Soc. of Plant Physiologists, Va.-Poly. Inst. and State Univ., Blacksburg, Va., June 25, 1978)] that P-IAA produced 2-4 times as many root primordia per leafy bean cutting (Top Crop) as did IAA. But as beans are herbaceous, this work suggests nothing regarding the effectiveness of P-IAA on woody cuttings, particularly on poor rooters, and it suggests nothing regarding the effectiveness of aryl esters of other auxins as rooting hormones.

SUMMARY

It is, accordingly, an object of the present invention to provide for improved adventitious root initiation.

It is another object of the present invention to overcome deficiencies in the prior art, such as deficiencies in the prior art indicated above.

It is a further object to provide improved, synthetic auxins.

It is yet another object to more effectively induce rooting in difficult to root species, including mature trees.

It is yet another object to provide for the economic propogation of mature trees.

It is a further object to provide a method of making improved auxins.

These and other objects of the invention are achieved by the synthesis* and use as rooting hormones of aryl esters and ethers of various auxins, more particularly of the phenol and hydroxyphenol esters of IAA, IBA and NAA, most preferably the latter two. These compounds have been shown to be substantially superior in promoting adventitious root formation in comparison with their corresponding free acids. The results of tests indicate potential commercial use of the phenol and 3-hydroxy phenol esters of IBA and NAA (e.g. 3HP-IBA, P-IBA and P-NAA) and of other aryl esters and ethers of auxins.

*The synthesis of one or more of these compounds was unsuccessfully attempted by Nekuda (1977, The synthesis of derivitives of indole-3-acetic acid; Master of science thesis. South Dakota School of Mines and Technology). One of us reported such synthesis (Giacoletto, 1978 "The synthesis of derivitives of indole-3-acetic acid II." Master of science thesis. South Dakota School of Mines and Technology—made available Sept. 13, 1978). These theses are hereby incorporated by reference.

DETAILED DESCRIPTION OF EMBODIMENTS

P-IAA is made in accordance with the present invention by the reaction of phenol, IAA and any suitable aryl or alkyl carbodiimide e.g. dicyclohexycarbodiimide, by first reacting the IAA and the imide and then mixing therewith the phenol. P-IBA was obtained in a similar manner by the reaction of phenol, IBA and dicyclohexylcarbodiimide. 3HP-IAA is made in a similar way using 3-hydroxyphenol as a starting reagent.

The key to the synthesis is the separation of the auxin aryl ester from the reaction medium. For such separation it is essential to use solvents of intermediate polarity such as ethers, e.g. diethyl ether or tetrahydrofuran, or chloroform. Strongly polar solvents such as alcohols will not work, nor will strongly non-polar solvents such as hydrocarbons. It is desirable to carry out the separation of low temperature, and the removal of impurities may require several stages.

Other aryl esters of auxins including P-NAA can be similarly made. The ethers can be made by reaction of the corresponding alcohol with a strong acid or by the Williamson synthesis.

The aryl esters of auxins are found to stimulate the initiation of adventitious root formation in cuttings to a much greater extent than previously known auxins. These materials may be used in the usual way by contacting the stem of the cutting with a suitable quantity of the aryl ester auxin at suitable concentration, and then placing the so-treated stem in a suitable rooting medium of spagnum moss, vermiculite, soil, sand, perlite, etc. until adequate rooting occurs, after which the rooted plant may then be potted; or alternatively the cuttings may be rooted in pots so no transplanting, prior to placement of the plant in its final location, is necessary.

The treating medium containing the aryl ester auxin may comprise any non-toxic diluant or carrier, including those conventionally used with rooting hormones. Thus, the composition may be solid, i.e. powdery, or it may be a liquid such as absolute or 95% ethanol. Regardless of the selection of the carrier, and any conventional carrier used in this field is suitable, it should be inert, i.e. non-toxic, to the plants. The active compounds are highly insoluble in water, and therefore where the carriers are liquid it is necessary that they first be dissolved in a solvent such as ethanol or other water miscible solvent and then mixed with water if water is to be used. The compounds may, however, be emulsified directly in water or a suitable buffer solution or they may be dissolved in a non-toxic water-immiscible solvent such as a light oil or a fat like lanolin, and then emulsified with a surface active agent in water or buffer solution. Normally water is not preferred, however, because it is desired that where a liquid carrier is used, that it evaporate quickly, and therefore ethanol is a preferred carrier. Solid carriers include talc, diatomaceous earth, various clays, etc.

The concentration of the auxin in the composition is subject to wide variation. The auxins are hormones and thus they are active at extremely low concentrations. In general, however, they are suitably used at concentrations of 0.00001 to 0.1 moles per liter, it being understood that the preferred concentration will vary depending on the length of treatment, longer treatments of the cutting with the auxin composition requiring lesser concentrations. However, as it is desirable from a commercial point of view to quick-dip the cuttings, it will be understood that concentrations towards the upper end of the range indicated above will normally be more suitable.

The present invention is particularly suitable for the rooting of woody, as opposed to herbaceous, plants; and it is particularly suitable in the rooting of "non-rooters" and "poor rooters" or "difficult-to-root" species (which are art recognized groups—see Audus, supra). Poor rooters include such commercially important species as Albies (firs), Picea (spruces), Populus, Quercus (oaks), Pinus, and landscaping plants such as Ilex (hollies) Juniperus, Kalmia (Laurels), Crape Myrtle, Cornus (dogwoods), Magnolias and Camellias. Non rooters include maples, douglas fir, pear, apple, beech, redwood, ash.

The compounds of the present invention have the following structures:

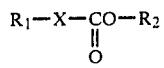

or

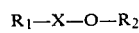

Wherein $R_1$ is

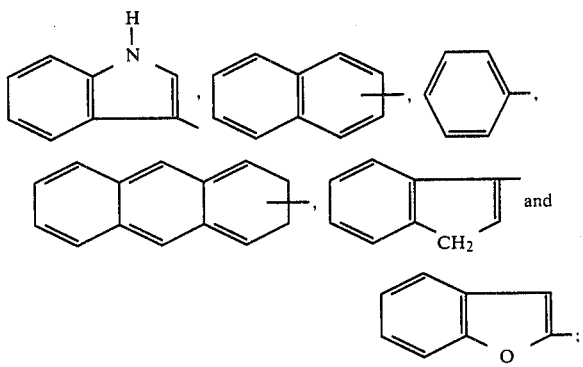

X is $(CH_2)_n$ wherein n is 1-3,

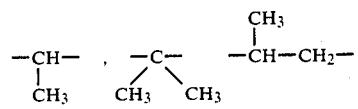

and $-O-CH_2-$; and $R_2$ is phenyl or substituted phenyl, including the residues of 3-hydroxyphenol, p-hydroxybenzoic acid, salicylic acid, gallic acid, cinnamic acid, p-hydroxycinnamic acid, caffeic acid, ferulic acid and sinapic acid.

Preferred compounds have the following formulas:

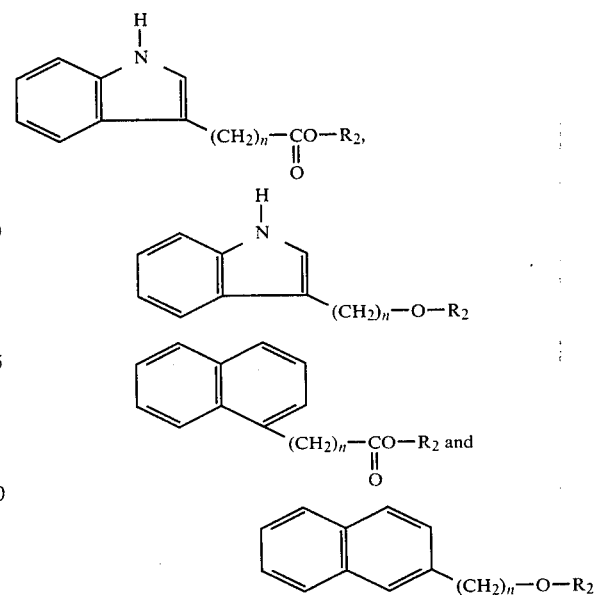

wherein $R_2$ is as defined above and most preferably phenyl or 3-hydroxyphenyl; and n is an integer of 1-3, preferably 1 to 3.

The most preferred compounds in accordance with the present invention are phenyl indole-3-butyrate (P-IBA); 3-hydroxyphenyl indole-3-acetate (3HP-1AA); and phenyl naphthalene acetate (P-IAA).

The following examples will illustrate the manner in which the invention can be practiced, it being understood that these examples are illustrative only and are not to be considered limiting:

EXAMPLE 1—Synthesis and Purification of Phenyl Indole-3-Acetate (P-IAA)

Tetrahydrofuran, dried over calcium hydride was used as the solvent. Prior to synthesis all reaction vessels were oven-dried. The following mole ratios were observed: one mole IAA: one mole phenol: one mole dicyclohexylcarbodiimide. Three one-hundredths mole (2.823 g.) phenol, 0.030 mole (5.256 g.) IAA, and 0.030 mole (6.190 g.) dicyclohexylcarbodiimide were each dissolved in a minimal amount of tetrahydrofuran in individual glass-stopped Erlenmeyer flasks. The IAA and the dicyclohexylcarbodiimide solutions were combined and allowed to react for 10 mins. at 20° C. This mixture was added to the phenol solution and permitted to react at room temperature for 36 hrs.

At the end of 36 hrs there was an abundant growth of needle-like white crystals in the flask. The solution was cooled to 0° C. and filtered. The crystals were washed with −5° C. tetrahydrofuran and the filtrates were combined. Combined filtrate was reduced to one-third the original volume by vacuum distillation and placed in a 0° C. refrigerator. Again, white crystals appeared and were filtered from solution. Volume reduction, cooling, crystallization, and filtration were performed a third time; the resulting filtrate had a volume of 8 to 10 ml.

Tetrahydrofuran was vacuum distilled from the mixture, leaving a honey-colored residue. This residue was dissolved in a minimal amount of warm absolute ethanol, allowed to cool, and then placed in a 0° C. refrigerator. A generous growth of light tan crystals appeared in three days; the crystals were washed with −10° C. ethanol and vacuum filtered using a Buchner funnel. Filtrate was again concentrated and placed back in the refrigerator.

At this point, the white needle-like crystals and the light-tan crystals were analyzed using an infrared spectrometer. The white crystals were identified as dicyclohexylurea by comparison to a known spectrum. The tan crystals gave an infrared scan identical to the phenyl product of the mixed anhydride synthesis and weighed 3.108 g. This represented a 41.2 percent yield. These crystals were recrystallized from absolute methanol and gave a m.p. of 71.0° to 71.1° C.

A new lot of the phenol ester was prepared using the dicyclohexylcarbodiimide procedure at the 0.03 mole level. After the third volume reduction and crystallization, the crude ester was dissolved in a minimal amount of absolute methanol, cooled, and filtered to remove residual dicyclohexylurea. Solution was concentrated and placed in a refrigerator (0° C.). An amorphous mass of orange-red crystals appeared within 48 hrs. Infrared analysis showed this to be P-IAA with some remaining dicyclohexylurea.

Silica gel was slurried with benzene and added to a chromatography column. The ester was dissolved in a minimal amount of benzene, placed in an addition funnel and run onto the packing; 200 ml of absolute methanol was used as the eluent under 5 to 10 psi nitrogen gas to increase flow rate. The light orange methanol fraction was collected, reduced in a flash-evaporator, and placed in a refrigerator (0° C.). Light orange crystals appeared within 24 hrs. The final yield was 2.791 gm representing a 39.5 percent yield. The melting point was 71° C. Anal. Calcd. for $C_{16}H_{13}O_2N$: C, 76.48%; H, 5.21%; N, 5.57%, Found: C, 76.29%; H, 5.33%; N, 5.47%.

Compound identify and purity for P-IAA (as well as 3HP-IAA and P-IBA produced as disclosed in following examples) was established as follows.

Quantitative determinations of carbon, hydrogen, nitrogen, and oxygen were performed by Galbraith Laboratories, Knoxville, TN. Infrared spectra were obtained using a Beckman, Model IR-10, double beam spectrophotometer. All samples were run as KBr discs at a scan speed of 14 minutes. Nuclear magnetic resonance spectra were run on a Varian A-60 spectrophotometer. Deuterated acetone was used as solvent for samples. Tetramethylsilane was the internal standard. Mass spectra were obtained using a Varian Mat CH5 Massenspektrometer, double-focusing, at Montana State University, Bozeman, Montana.

High performance liquid chromatography of the purified product was performed with Waters Associates equipment, including two 6000A pumps, 660 solvent programmer, U6K injector, 440 detector (280 nn filter), and 3.9 cm×30 cm$\mu$Bondapak-$C_{18}$ column, which was maintained at 18±0.5° C. Data were gathered with a Honeywell dual pen recorder and a Varian CDS 11 integrator, which was programmed to calculate concentrations by the internal standard-relative response factor method. The solvent was acetonitrile-five percent acetic acid in glass distilled water (25/75 by volume) at a flow rate of one ml per min.

Sample purity was verified by hydrolyzing P-IAA with 1.5 normal KOH to yield IAA and phenol. IBA was used as the internal standard in determining the concentrations of IAA in the hydrolyzate and in unhydrolyzed P-IAA solutions. The hydrolyzate, as chromatographed, contained 325 nMoles per ml of IAA, and 410 nMoles per ml of IBA. Purity of P-IAA, after correction for IAA contained therein (4 percent), was about 93 percent.

EXAMPLE 2—Synthesis and Purification of Phenyl Indole-3-Butyrate (P-IBA)

Phenol (0.46 g., 0.005 mole), dicyclohexylcarbodiimide (1.01 g, 0.005 mole) and indole-3-butyric acid (1.00 gm. 0.005 mole) were dissolved in minimal amounts of tetrahydrofuran in individual glass-stoppered Erlenmeyer flasks. Indole-3-butyric acid and dicyclohexylcarbodiimde solutions were mixed together and allowed to react for 15 minutes. The phenol solution was then added and the mixture allowed to react for 48 hours at room temperature. The mixture was then cooled in a refrigerator (0° C.). Dicyclohexylurea crystals which formed were filtered, washed with cold tetrahydrofuran, and the filtrate reduced in volume. Filtration, washing, and volume reduction were repeated four times.

Cold anhydrous ethyl ether was then added to the resulting solution to remove any remaining dicyclcohexylurea. The solution was filtered, washed with cold ethyl ether, reduced in volume, and placed in a refrigerator (0° C.). This process was repeated with the resulting solution being placed in a refrigerator (−20° C.) for 48 hours. Clear, light-yellow, plate-like crystals were collected, washed with cold ethyl ether and allowed to air-dry. The yield was 0.237 g (17.0% yield). Melting point is 71° C.

The procedure was repeated at a 0.015 mole level of reactants which yielded 0.608 g (14.5% yield). Anal. Calcd. for $C_{18}H_{17}O_2N$ C, 77.42% H, 6.09%; O, 11.47% N, 5.02%. Found: C, 77.34%; H, 6.51%; O, 11.10%; N, 4.88% (ave). Purity of this lot was thus about 95 percent.

A second lot was not purified as highly as the first lot. High performance liquid chromatography indicated 73 percent purity, after correction for 4 percent contamination with IBA.

EXAMPLE 3—Synthesis and Purification of 3-Hydroxyphenyl Indole-3-Acetate (3HP-IAA)

The dicyclohexylcarbodiimide procedure was used to synthesize the 3-hydroxyphenyl ester using 0.03 moles of starting compounds.

Crude orange-brown product was recrystallized from absolute ethanol. It was then dissolved in a minimal amount of tetrahydrofuran, placed on a silica gel column, and eluted with 100 ml of tetrahydrofuran. The solution was reduced in volume, cooled, and allowed to crystallize. The product, still orange-brown in color, was placed in 100 ml of hot ethanol with 1 g of Nuchar activated carbon for 5 minutes. The hot solution was filtered, reduced in volume and placed in a refrigerator (0° C.). Off-white colored crystals appeared within 24 hrs. These were collected and air-dried. Infrared analysis showed no evidence of dicyclohexylurea. The yield was 0.750 g representing a 9.4 percent yield. Melting point is 141 C., Anal. Calcd. for $C_{16}H_{13}O_3N$: C, 71.90%; H, 4.87% O, 17.98% N, 5.24%. Found: C, 73.39; H. 4.86%; 0.15%; N, 6.52% (ave.)

High performance liquid chromatography indicated 86 percent purity, with less than one percent IAA present.

EXAMPLE 4—Rooting Trials Comparing Phenyl and 3-Hydroxyphenyl Indole-3-Acetate with Indole-3-Acetic Acid and Ethyl Indole-3-Acetate Pinto bean (*Phaseolus vulgaris* cv Top Crop) plants were grown from seed in a growth chamber (18 hr. days, 22° C. days, 20° C. nights) in perlite. Plants were watered daily with deionized water until emergence, then with complete nutrient solution. Cuttings were prepared (about 9 days after planting) from plants with primary leaves of from 3.5 to 4.5 cm long. The hypocotyl was severed 5 cm below the cotyledons, which were removed.

Treatment solutions were prepared in 10 mM MES-*—NaOH buffer, pH 6.0, by dissolving P-IAA, 3HP-IAA, IAA and ethyl indole-3-acetate (E-IAA) in absolute ethanol at 1000 times the desired final concentration. Purity of P-IAA and 3HP-IAA were 93 percent and 86 percent, respectively. Dilution with buffer yielded the desired concentrations as shown in Tables 1, 2, and 3. Thus, treatment solutions, and control solution, also contained 1 ml of absolute ethanol (or 0.1%) per liter.
* (2 [N-morpholino] ethane sulfuric acid).

Cuttings (5) were placed in vials containing 20 ml of treatment solution. Each treatment was replicated 5 times within a run. Runs were performed twice. Vials containing cuttings were placed in shallow plastic pans in an incubator (18 hr days, 25° C. day and night). After 24 hrs. treatment solutions were removed from vials, and replaced with double deionized water after the cuttings and vials were rinsed. Water in vials was replaced each 24 hrs for the duration of an experiment.

Root primordia on the hypocotyl of each cutting were counted three days after the treatment began. Cuttings were removed from the vial, placed in a small water-filled test tube, and examined under a reading glass. The cuttings were returned to their original vials for two additional days. Then the number of roots that had elongated to two or more mm were counted on each hypocotyl as described above. Cuttings were then discarded.

Results showed that P-IAA treated cuttings produced more root primordia per cutting than did cuttings treated with about equal concentrations of IAA (Table 1). On a molar basis, P-IAA treatment was at least 10 times as effective as IAA treatment; treatment with 0.2 $\mu$Molar P-IAA yielded about 27 root primordia per cutting whereas 10 times the concentration of IAA (2.0 $\mu$Molar) yielded only about 23 primordia per cutting.

TABLE 1

Influence of phenyl indole-3-acetate on adventitious root initiation and elongation by bean cuttings.

| Treatment | Concentration* ($\mu$Molarity) | x Primordia ± S.E.** Per Cutting | x Roots ± S.E.** per Cutting |
|---|---|---|---|
| Control | — | 7.96 ± 0.51 | 3.73 ± 0.57 |
| IAA | 0.2 | 13.78 ± 0.87 | 2.46 ± 0.44 |
| IAA | 2.0 | 22.50 ± 1.30 | 3.88 ± 0.62 |
| P-IAA | 0.2 | 26.92 ± 1.22 | 9.24 ± 0.98 |
| P-IAA | 2.0 | 35.04 ± 1.28 | 10.29 ± 0.98 |

*Not corrected for 7% impurity in P-IAA
**S.E. = standard error of the mean

Root development by P-IAA treated cuttings at both concentrations also greatly exceeded that of IAA treated cuttings (Table 1). At 0.2 $\mu$Molar, P-IAA treated cuttings had 276 percent more elongated roots than did cuttings that were treated with IAA; at 2:0 $\mu$Molar, the percentage increase was 165 in comparison with IAA treated cuttings.

Results obtained with 3HP-IAA were essentially the same as those obtained with P-IAA (Table 2). 3HP-IAA treatment at both concentrations produced more root primorida per cutting (from 41 to 73 percent more) and more elongated roots per cutting (from 99 to 124 percent more) than did IAA treatment at a somewhat higher concentration.

TABLE 2

Influence of 3-hydroxyphenyl indole-3-acetate adventitious root initiation of elongation by bean cuttings.

| Treatment | Concentration* ($\mu$Molarity) | x Primordia ± S.E.** Per Cutting | x Roots ± S.E.** Per Cutting |
|---|---|---|---|
| Control | — | 7.02 ± 0.44 | 1.18 ± 0.27 |
| IAA | 0.2 | 13.20 ± 0.77 | 3.08 ± 0.49 |
| IAA | 2.0 | 21.10 ± 1.15 | 7.40 ± 0.97 |
| 3HP-IAA | 0.17 | 22.90 ± 0.98 | 6.90 ± 0.77 |
| 3HP-IAA | 1.72 | 29.72 ± 1.04 | 14.72 ± 1.21 |

*Corrected for 86 percent of 3HP-IAA.
**S.E. = standard error of the mean

P-IAA treatment proved substantially more effective in inducing primordium initiation than did the alkyl ester, E-IAA (Table 3). E-IAA treatment was little, if any, more effective than treatment with IAA.

TABLE 3
Influence of ethyl indole-3-acetate on adventitious root initiation and elongation by bean cuttings.

| Treatment | Concentration* (μMolarity) | x̄ Primordia ± S.E.** Per cutting | x̄ Roots ± S.E.** per cutting |
|---|---|---|---|
| Control | — | 6.08 ± 0.35 | 1.74 ± 0.27 |
| E-IAA | 0.2 | 16.48 ± 0.97 | 5.88 ± 0.54 |
| P-IAA | 0.2 | 27.96 ± 1.05 | 5.86 ± 0.47 |
| IAA | 0.2 | 14.94 ± 0.97 | 3.48 ± 0.68 |

*Not corrected for 93% purity of P-IAA
**S.E. = standard error of the mean

EXAMPLE 5—Rooting Trials Comparing Phenyl Indole-3-Buytrate to Indole-3-Butyric Acid Three runs were carried with jack pine (*Pinus banksiana*) cuttings in order to test the effect of P-IBA.**
** IAA treatment is ineffective for induction of adventitious root initiation in cuttings of woody species, such as jack pine. In preliminary trials, P-IAA treatment similarly was found to be ineffective. However, IBA treatment has proven effective in inducing adventitious root iniatiation in cuttings of jack pine. Thus, jack pine was used to test the influences of P-IBA.

Jack pine cuttings were prepared from seedlings that were grown from a single lot of open pollinated seed in a growth chamber (18 hr. days, 22° C. days, 20° C. nights). Cuttings were prepared by severing the hypocotyl just above the root collar with a sharp razor blade. Cuttings in all experiments were rooted in sand-perlite (2:1 by volume) in heated (23° to 25° C.) greenhouse propagation benches under intermittent mist. Supplementary incandescent illumination (150 W, PAR-38 lamps) extended the daylength to 18 hrs.

In run #1, cuttings were made from 127-day-old seedlings. Three replications of 25 cuttings each were used per treatment (control, IBA, or P-IBA). Cuttings were treated with absolute ethanol (control), 1.0 mg IBA per ml absolute ethanol (4.92 mMolar IBA), or 1.0 mg P-IBA per ml absolute ethanol (3.58 mMolar P-IBA) by the quick dip method (Hartmann et al., 1975). Purity of this lot of P-IAA was about 95 percent. Rooting date were collected after 59 days in the rooting bed.

In run #2, cuttings were made from 138-day-old seedlings. Each treatment (control, IBA, or P-IBA) contained 24 cuttings. Cuttings were treated with 10 mMolar MES-NaOH buffer, pH 6.0 (control), 25 μg IBA per ml buffer (123.0 μMolar IBA), or 25 μg P-IBA per ml buffer (89.5 μMolar P-IBA). Purity of this lot of P-IBA was about 95 percent. Twelve cuttings were placed with their bases in a 100 ml beaker that contained 40 ml of appropriate treatment solution and 5 glass marbles. Cuttings were then placed in an illuminated incubator (18 hr day, 25±0.5° C. day and night) until they had taken up all of the solution (overnight to 24 hrs). Cuttings were then planted in the propagation bench. Rooting data were collected after 45 days.

In run #3, cuttings were made from 148-day-old seedlings. Three replications of 48 cuttings each were used per treatment (control, IBA, or P-IBA). Cuttings were treated as in run #2, but with deionized water, IBA (10.15 μg per ml deionized water, 50 μMolar in IBA), or P-IBA (14.00 μg per ml deionized water, 36.5 μMolar in P-IBA after correction for 73 percent purity of this lot of P-IBA). Rooting data were collected 38 days after cuttings were planted in the propagation bench.

The results of all three runs indicated that 11 to 12 percent more cuttings initiated roots when treated with P-IBA in comprison with IBA (Tables 4, 5 and 6). Neither the number of roots per rooted cutting, nor length of the longest root per rooted cutting differed significantly between treatments. In runs 1, 2 and 3 on a molar basis, about 27 percent less P-IBA than IBA was used to treat cuttings, which indicates substantially greater effectiveness of P-IBA.

TABLE 4
Influence of phenyl indole-3-butyrate (quick dip) on adventitious root initiation and elongation by jack pine cuttings.

| Treatment | Concentration* (mMolarity) | No. Rooted Cuttings (%) | x̄ Roots ± S.E.** Per Rooted Cutting | x̄ length ± S.E.** of longest Root per Rooted Cutting (mm) |
|---|---|---|---|---|
| Control | — | 66 | 1.50 ± 0.19 | 26.30 ± 3.69 |
| IBA | 4.92 | 83 | 2.84 ± 0.27 | 43.94 ± 3.03 |
| P-IBA | 3.58 | 94 | 2.94 ± 0.23 | 37.47 ± 3.46 |

*Concentrations shown represent amounts of one mg of each compound per ml, and were not corrected for 95% of purity.
**S.E. = standard error of the mean

TABLE 5
Influence of phenyl indole-3-butyrate (buffered soak) on adventitious root initiation and elongation by jack pine cuttings.

| Treatment | Concentration* (μMolarity) | No. Rooted Cuttings (percent) | x̄ Roots ± S.E.** Per Rooted Cuttings |
|---|---|---|---|
| Control | — | 68 | 1.76 ± 0.26 |
| IBA | 123.0 | 72 | 8.83 ± 1.83 |
| P-IBA | 89.5 | 84 | 9.67 ± 1.41 |

*Concentrations represent amounts of 25μg of each compound per ml, and were not corrected for 95% purity of P-IBA.
**S.E. = standard error of the mean.

TABLE 6
Influence of phenyl indole-3-butyrate (water-soak) on adventitious root initiation and elongation by jack pine cuttings.

| Treatment | Concentration* (μMolarity) | No. Rooted Cuttings (%) | x̄ Roots ± S.E.** Per Rooted Cutting | x̄ length ± S.E.** of longest Root per Rooted Cutting (mm) |
|---|---|---|---|---|
| Control | — | 54.2 | 2.60 ± 0.22 | 21.67 ± 2.31 |
| IBA | 50.0 | 82.1 | 5.99 ± 0.43 | 54.20 ± 3.05 |
| P-IBA | 36.5 | 92.9 | 6.15 ± 0.39 | 54.42 ± 3.11 |

*Corrected for 73 percent purity of P-IBA.
**S.E. = standard error of the mean

EXAMPLE 6—Enzymatic Hydrolysis

Prevailing evidence suggests that esters of auxins, such as methyl or ethyl indole-3-acetate, must be hydrolyzed before they become physiologically active. Thus, it was assumed that P-IAA, 3HP-IAA, and P-IBA were enzymatically hydrolyzed in vivo to yield the free acid and corresponding simple phenolic. The supposition was explored by preparing enzyme extracts of bean hypocotyl tissue and jack pine hypocotyl tissue, and exposing either P-IAA solutions to the bean extract, or P-IBA solutions to the jack pine extract. Product identity and rates of hydrolysis were determined by co-chromatographing standards and hydrolysates with a high performance liquid chromatograph (see above).

In Experiment 1, hypocotyls were removed from the standard bean plants; and fast frozen (−85° C.), lyophilized, and milled to pass the 20-mesh screen of a Wiley mill. Tissue (100 mg) was homogenized in a total volume of 3.0 ml of 10 mMolar MES-NaOH buffer, pH 6.0. Extracts were centifuged (30,000 xg, 30 min), and the pellet was discarded (Haissig et al. 1972). One ml of bean extract was added to 1.0 ml of P-IAA solution (2.0 mMolar in ethanol) and 8.0 ml of 10 mMolar MES-NaOH buffer, pH 6.0. Boiled bean extract was used in the control. Reaction mixtures were chromatographed just after addition of extract, and periodically for about 24 hrs. Chromatography solvent was absolute methanol-5 percent acetic acid in glass distilled water (70:30 by volume) at a flow rate of 5.0 ml per min.

In Experiment 2, hypocotyls of jack pine plants were similarly processed, except 100 mg of insoluble polyvinylpyrolidone (PVP) was added before homogenization of each 100 mg sample of tissue, and bufferee contained 10 mMolar dithioerythintol, i.e. DTE (Haissig and Schipper 1975). One ml of diluted (1:15 by volume with buffer) extract was added to 1.0 ml of P-IBA solution (895.0 $\mu$Molar), and 8.0 ml of 10 mMolar MES-NaOH buffer, pH 6.0, containing 10 mMolar DTE. The control contained boiled extract. Reaction mixtures were chromatographed just after addition of extract, and at several subsequent times, for about 24 hrs. Chromatography solvent was acetonitrile-5 percent acetic acid in glass distilled water (45:55 by volume) at a flow rate of 0.5 ml per min.

Results indicated that bean extract contains one or more aryl ester hydrolases (E.C. 3.1.1.2) that hydrolyze P-IAA to IAA, phenol, and at least one unidentified compound. Similarly, jack pine extracts contained one or more aryl ester hydrolases that hydrolyzed P-IBA to IBA, phenol, and at least one unidentified compound. Results show incomplete hydrolysis of P-IBA after about 24 hrs when enzyme extracts were diluted before use. However, complete hydrolysis was readily obtained in only a few minutes when undiluted enzyme extracts were used. Thus, it is possible that the enhanced rooting of cuttings that were treated with P-IAA, 3HP-IAA or P-IBA was due to an unidentified product of hydrolysis.

EXAMPLE 7—Control Runs

In run 1, the standard bean cuttings were treated with P-IAA, IAA, phenol, or IAA and phenol by methods described in Example 1. Rooting data were collected as was done before.

In run 2, P-IAA solutions were hydrolyzed with the bean extract (as above), appropriately diluted, and used to treat the standard bean cuttings in the usual manner. Rooting data were collected as was done before.

The two check experiments established that the P-IAA effect on adventitious root initiation could not be replaced by phenol, IAA and phenol combined (Table 7), or any unidentified product of enzymic hydrolysis (Table 8)

TABLE 7

Influence of phenol and phenol plus indol-3-acetic acid on adventitious root initiation and elongation by bean cuttings.

| Treatment | Concentration* ($\mu$Molarity) | $\bar{x}$ Primordia ± S.E.** per Cutting | $\bar{x}$ Roots ± S.E.** per Cutting |
|---|---|---|---|
| Control | — | 9.36 ± 0.62 | 2.76 ± 0.39 |
| P-IAA | 0.2 | 31.26 ± 1.23 | 12.70 ± 1.14 |
| IAA | 0.2 | 13.72 ± 0.74 | 6.60 ± 0.55 |
| Phenol | 0.2 | 9.68 ± 0.58 | 3.06 ± 0.47 |

TABLE 7-continued

Influence of phenol and phenol plus indol-3-acetic acid on adventitious root initiation and elongation by bean cuttings.

| Treatment | Concentration* ($\mu$Molarity) | $\bar{x}$ Primordia ± S.E.** per Cutting | $\bar{x}$ Roots ± S.E.** per Cutting |
|---|---|---|---|
| IAA + Phenol | 0.2 | 12.50 ± 0.70 | 5.06 ± 0.50 |

*Not corrected for 93 percent purity of P-IAA.
**S.E. = standard error of the mean In run 1, P-IAA treated cuttings showed the largest rooting response, which showed the relative ineffectiveness of phenol alone or in combination with IAA (Table 7). In run 2, treatment of cuttings with P-IAA that had been exposed to boiled (enzymatically inactive extract) yielded a much greater rooting response than did treatment of cuttings with P-IAA that had been hydrolyzed by enzymes in unboiled extract. Treatment with P-IAA hydrolysate solutions yielded result similar to those obtained in earlier experiments after IAA treatment (Table 8).

TABLE 8

Influence of enzymically hydrolyzed phenyl indole-3-acetate on adventitious root initiation and elongation by bean cuttings.

| Treatment | Concentration* ($\mu$Molarity) | $\bar{x}$ Primordia ± S.E.** per Cutting | $\bar{x}$ Roots ± S.E.** per Cutting |
|---|---|---|---|
| Control | — | 7.86 ± 0.58 | 3.22 ± 0.35 |
| P-IAA (hydrolyzed) | 0.2 | 12.46 ± 0.94 | 7.22 ± 0.70 |
| P-IAA | 0.2 | 22.94 ± 1.21 | 16.88 ± 1.17 |

*Not corrected for 93 percent purity of P-IAA
**S.E. = standard error of the mean.

The following conclusions are reached:

1. It is possible to synthesize aryl esters of indole-3-acetic acid, indole-3-butyric acid, and similar auxins such as indole-3 propionic acid, napthalene acetic acid, and compounds with similar structural formulas.

2. Phenyl indole-3-acetate was substantially more effective in inducing adventitious root primordium initiation than the alkyl ester, ethyl indole-3-acetate. The alkyl ester was little, if any, more effective than the free acid.

3. The aryl esters that were tested enhanced adventitious root initiation in comparison with their free acids. The phenyl ester of indole-3-butyric acid enhanced adventitious root initiation in cuttings of a woody species (jack pine) in comparison with indole-3-butyric acid, which is the auxin used in most proprietary chemical formulations for rooting cuttings of woody plants. Conventional methods of treating cuttings with auxins (basal soak or quick dip), when tested with phenyl indole-3-butyrate, yielded a 10 to 11 percent increase in the number of rooted cuttings. It is therefore believed that other aryl esters and ethers may be synthesized which are as or more effective in inducing adventitious root initiation than phenyl or 3-hydroxyphenyl esters.

4. The aryl esters are apparently taken into the cuttings in an unhydrolyzed form. However, subsequent physiological action in inducing root initiation probably requires enzymatic hydrolysis to yield the free acid of the auxin.

5. Efficiency of given compounds in inducing adventitious root initiation has been a long standing test of auxin activity. Thus, aryl esters of naphthalene and indole auxins appear to be more effective than the free acids or alkyl esters in modification of other important physiological processes which auxins are used to control, initiate, or terminate.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A composition for stimulating adventitious root formation in difficult-to-root cuttings, comprising:

an amount sufficient to stimulate adventitious root formation of a compound of the formula

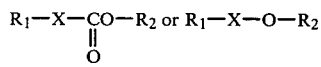

wherein $R_1$ is

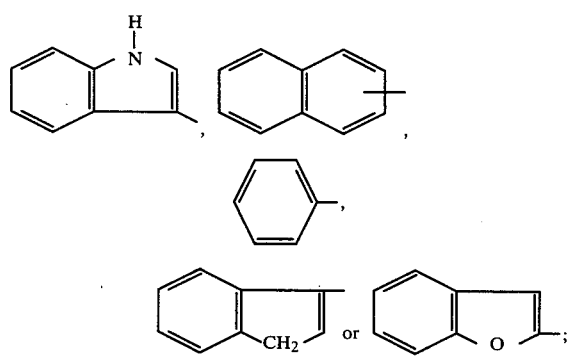

X is $(CH_2)_n$ wherein n is 1–3,

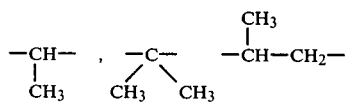

or $-O-CH_2-$; and $R_2$ is phenyl or substituted phenyl, with the proviso that n is not 1 when $R_1$ is

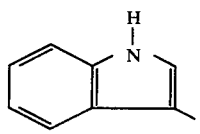

and $R_2$ is phenyl; and a volatile or inert non-toxic carrier.

2. A composition in accordance with claim 1 wherein said compound is of the formula:

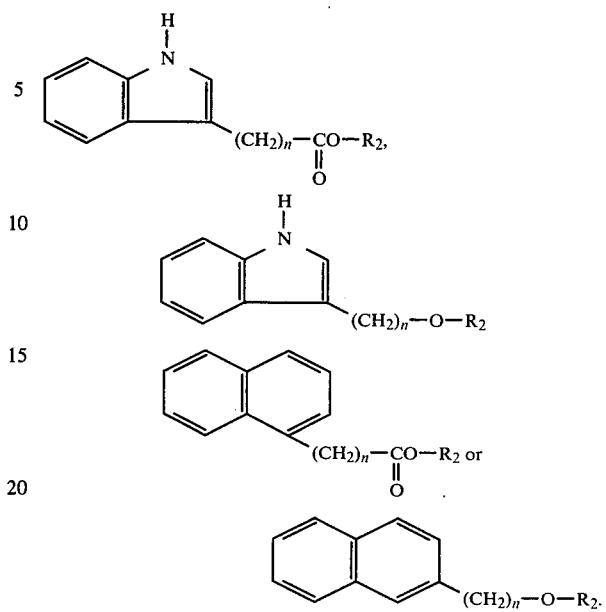

3. A composition in accordance with claim 1 wherein $R_2$ is phenyl or is a residue of 3-hydroxyphenol, p-hydroxybenzoic acid, salicylic acid, gallic acid, cinnamic acid, p-hydroxycinnamic acid, caffeic acid, ferulic acid or sinapic acid.

4. A composition for stimulating adventitious root formation in difficult-to-root cuttings, comprising:

an amount sufficient to stimulate adventitious root formation of a compound selected from the group consisting of P-IBA, 3HP-IBA, 3HP-IAA, P-NAA and 3HP-NAA; and a volatile or inert non-toxic carrier.

5. A method of stimulating adventitious root formation in cuttings of difficult-to-root plants, comprising:

taking a cutting from a said plant; contacting said cutting adjacent and over the location of the cut with an amount sufficient and for a time sufficient to stimulate adventitious root formation of a compound of the formula:

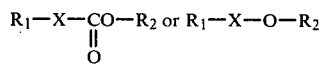

wherein $R_1$ is

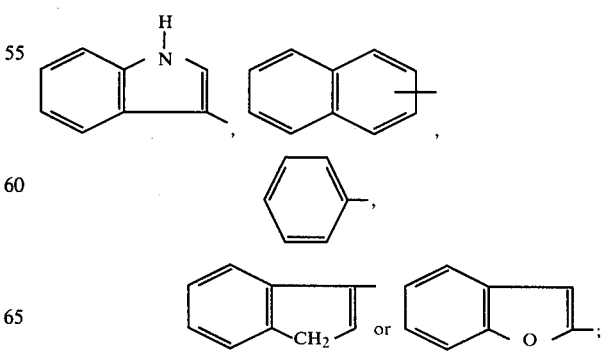

X is $(CH_2)_n$ wherein n is 1–3,

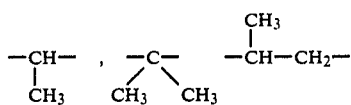

or —O—CH$_2$—; and R$_2$ is phenyl or substituted phenyl, with the proviso that n is not 1 when R$_1$ is

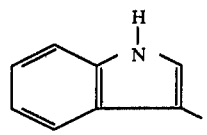

and R$_2$ is phenyl; and placing said cutting into a rooting medium for a time sufficient for said cutting to develop roots.

6. A method in accordance with claim 5 wherein said cutting is dipped into a composition of said compound in a volatile or inert non-toxic carrier.

7. A method in accordance with claim 5 wherein said compound is selected from the group consisting of P-IBA, 3HP-IBA, 3HP-IAA, P-IAA and 3HP-NAA.

* * * * *

UNITED STATES PATENT AND TRADEMARK OFFICE
CERTIFICATE OF CORRECTION

PATENT NO. : 4,297,125

DATED : October 27, 1981

INVENTOR(S) : Bruce E. Haissig, Jack R. Gaines and Glen Giacoletto

It is certified that error appears in the above—identified patent and that said Letters Patent is hereby corrected as shown below:

ON THE TITLE PAGE, Item (73), should read

[73] Assignee: The United States of America, as represented by the Secretary of Agriculture, Washington, D. C., and South Dakota School of Mines & Technology, Rapid City, South Dakota.

Signed and Sealed this

Twenty-first Day of December 1982

[SEAL]

Attest:

Attesting Officer

GERALD J. MOSSINGHOFF

Commissioner of Patents and Trademarks